US010451521B2

(12) United States Patent
Otero et al.

(10) Patent No.: US 10,451,521 B2
(45) Date of Patent: Oct. 22, 2019

(54) SYSTEMS AND METHODS FOR INSPECTING BLADES OR VANES IN TURBOMACHINERY

(71) Applicant: General Electric Company, Schenectady, NY (US)

(72) Inventors: Elena Otero, Baden (CH); Thomas Morris, Baden (CH); Christoph Hurzeler, Baden (CH)

(73) Assignee: General Electric Company, Schenectady, NY (US)

( * ) Notice: Subject to any disclaimer, the term of this patent is extended or adjusted under 35 U.S.C. 154(b) by 257 days.

(21) Appl. No.: 15/635,626

(22) Filed: Jun. 28, 2017

(65) Prior Publication Data

US 2019/0003925 A1    Jan. 3, 2019

(51) Int. Cl.
*G01M 15/02* (2006.01)
*F04D 27/00* (2006.01)
(Continued)

(52) U.S. Cl.
CPC ........... *G01M 15/02* (2013.01); *F01D 21/003* (2013.01); *F04D 27/001* (2013.01); *G01M 15/14* (2013.01); *G01N 29/225* (2013.01); *G01N 29/265* (2013.01); *F01D 5/12* (2013.01); *F01D 9/02* (2013.01); *F04D 29/324* (2013.01); *F04D 29/542* (2013.01); *F05D 2220/32* (2013.01);
(Continued)

(58) Field of Classification Search
CPC ..... G01M 15/02; G01M 15/14; F04D 27/001; F04D 29/324; F04D 29/542; F01D 21/003; F01D 5/12; F01D 9/02; F05D 2220/32; G01N 29/041; G01N 27/90; G01N 2291/2693

USPC .... 73/865.8, 618–644, 112.01; 324/228–243
See application file for complete search history.

(56) References Cited

U.S. PATENT DOCUMENTS 7,543,512 B2 * 6/2009 Smith ..................... E21B 47/01
                                                      73/865.8
8,042,399 B2 * 10/2011 Pasquali .............. G01N 29/225
                                                      73/622
(Continued)

FOREIGN PATENT DOCUMENTS

EP          1227316 A2     7/2002
EP          2345881 A1     7/2011
(Continued)

OTHER PUBLICATIONS

International Search Report and Written Opinion, PCT/US2018/034515, dated Dec. 24, 2018 (12 pp.).
International Search Report and Written Opinion issued in connection with corresponding PCT Application No. PCT/US2018/034515 dated Dec. 24, 2018.

*Primary Examiner* — Robert R Raevis
(74) *Attorney, Agent, or Firm* — Eversheds Sutherland (US) LLP (57) ABSTRACT

A scanner for inspecting a component is disclosed. The scanner may include a main body having a clamp attachable to the component, a first arm moveably attached to the main body, a first probe attached to the first arm, a first axial actuator in mechanical communication with the first arm, a second arm moveably attached to the main body, a second probe attached to the second arm, a second axial actuator in mechanical communication with the second arm, and a radial actuator in mechanical communication with the first arm and the second arm.

22 Claims, 13 Drawing Sheets

(51) Int. Cl.
  *F01D 21/00*   (2006.01)
  *G01M 15/14*   (2006.01)
  *G01N 29/22*   (2006.01)
  *G01N 29/265*  (2006.01)
  *F04D 29/32*   (2006.01)
  *F04D 29/54*   (2006.01)
  *F01D 5/12*    (2006.01)
  *F01D 9/02*    (2006.01)
  *G01N 29/04*   (2006.01)
  *G01N 27/90*   (2006.01)

(52) U.S. Cl.
  CPC ...... *F05D 2260/80* (2013.01); *F05D 2260/83* (2013.01); *G01N 27/90* (2013.01); *G01N 29/041* (2013.01); *G01N 2291/2693* (2013.01)

(56) References Cited

U.S. PATENT DOCUMENTS

| | | |
|---|---|---|
| 8,347,746 B2 | 1/2013 | Hafenrichter et al. |
| 2011/0178727 A1 | 7/2011 | Hafenrichter et al. |
| 2013/0135457 A1 | 5/2013 | Kell et al. |
| 2016/0010505 A1 | 1/2016 | Moore et al. |
| 2016/0202093 A1 | 7/2016 | Stanton et al. |

FOREIGN PATENT DOCUMENTS

| | | |
|---|---|---|
| EP | 2700811 A1 | 2/2014 |
| EP | 2727843 A2 | 5/2014 |
| WO | 2006/101586 A1 | 9/2006 |

\* cited by examiner

SYSTEMS AND METHODS FOR INSPECTING BLADES OR VANES IN TURBOMACHINERY

FIELD

The disclosure relates generally to turbomachinery and more particularly relates to systems and methods for inspecting blades or vanes in turbomachinery.

BACKGROUND

Turbomachinery components, such as blades and vanes, are difficult to inspect due to space restrictions. Current techniques for accessing and inspecting the blades and vanes include at least partially dismantling the turbomachinery. This can be time consuming and costly. Consequently, there is a need to provide more extensive and regular integrity assessments of the turbomachinery components that are affordable and feasible.

BRIEF DESCRIPTION

According to an embodiment, there is disclosed a scanner for inspecting a component. The scanner may include a main body having a clamp attachable to the component, a first arm moveably attached to the main body, a first probe attached to the first arm, a first axial actuator in mechanical communication with the first arm, a second arm moveably attached to the main body, a second probe attached to the second arm, a second axial actuator in mechanical communication with the second arm, and a radial actuator in mechanical communication with the first arm and the second arm.

According to another embodiment, there is disclosed a scanner for inspecting a component. The scanner may include a main body having a clamp attachable to a trailing edge of the component, a first flexible arm moveably attached to the main body about a first side of the component, and a first probe pivotally attached to the first flexible arm. The first probe may be configured to slide along the first side of the component. A first axial actuator may be in mechanical communication with the first flexible arm. The scanner also may include a second flexible arm moveably attached to the main body about a second side of the component, with a second probe pivotally attached to the second flexible arm. The second probe may be configured to slide along the second side of the component. A second axial actuator may be in mechanical communication with the second flexible arm. In addition, a radial actuator may be in mechanical communication with the first flexible arm and the second flexible arm.

Further, according to another embodiment, there is disclosed a method for inspecting a component. The method may include positioning a main body adjacent to the component, moving a first arm with a first probe and a second arm with a second probe in a radial direction with a radial actuator, moving the first arm and the first probe in an axial direction with a first axial actuator, and moving the second arm and the second probe in the axial direction with a second axial actuator.

Other embodiments, aspects, and features of the disclosure will become apparent to those skilled in the art from the following detailed description, the accompanying drawings, and the appended claims.

BRIEF DESCRIPTION OF THE DRAWINGS

Reference will now be made to the accompanying drawings, which are not necessarily drawn to scale.

DETAILED DESCRIPTION

The systems and methods described herein may be used to inspect blades or vanes (or any other component) in a turbomachine. The blades or vanes may be disposed in a compressor or a turbine. Any device with blades or vanes may utilize the systems and methods disclosed herein to inspect the blades or vanes. In some instances, the turbomachine may be a gas turbine engine. Any industrial or aviation turbomachine may be used.

Figure 1:
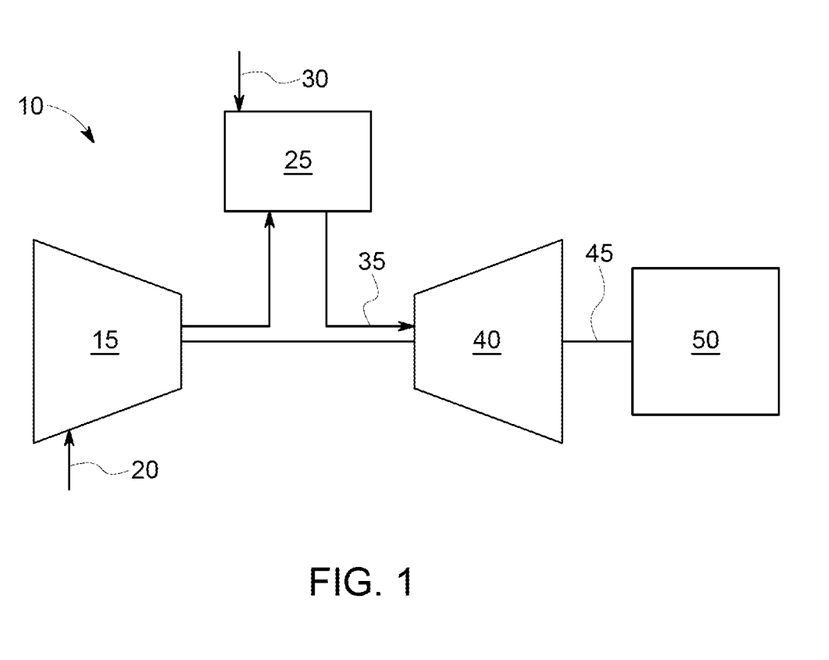
FIG. 1 depicts of an example gas turbine engine according to an embodiment.

Referring now to the drawings, in which like numerals refer to like elements throughout the several views, FIG. 1 depicts a schematic view of an example gas turbine engine 10 as may be used herein. The gas turbine engine 10 may include a compressor 15. The compressor 15 compresses an incoming flow of air 20. The compressor 15 delivers the compressed flow of air 20 to a combustor 25. The combustor 25 mixes the compressed flow of air 20 with a compressed flow of fuel 30 and ignites the mixture to create a flow of combustion gases 35. Although only a single combustor 25 is shown, the gas turbine engine 10 may include any number of combustors 25. The flow of combustion gases 35 is in turn delivered to a turbine 40. The flow of combustion gases 35 drives the turbine 40 so as to produce mechanical work. The mechanical work produced in the turbine 40 drives the compressor 15 via a shaft 45 and an external load 50 such as an electrical generator and the like.

The gas turbine engine 10 may use natural gas, various types of syngas, and/or other types of fuels. The gas turbine engine 10 may be any one of a number of different gas turbine engines offered by General Electric Company of Schenectady, N.Y., including, but not limited to, those such as a 7 or a 9 series heavy duty gas turbine engine and the like. The gas turbine engine 10 may have different configurations and may use other types of components. Other types of gas turbine engines also may be used herein. Multiple gas turbine engines, other types of turbines, and other types of power generation equipment also may be used herein together.

Figure 2:
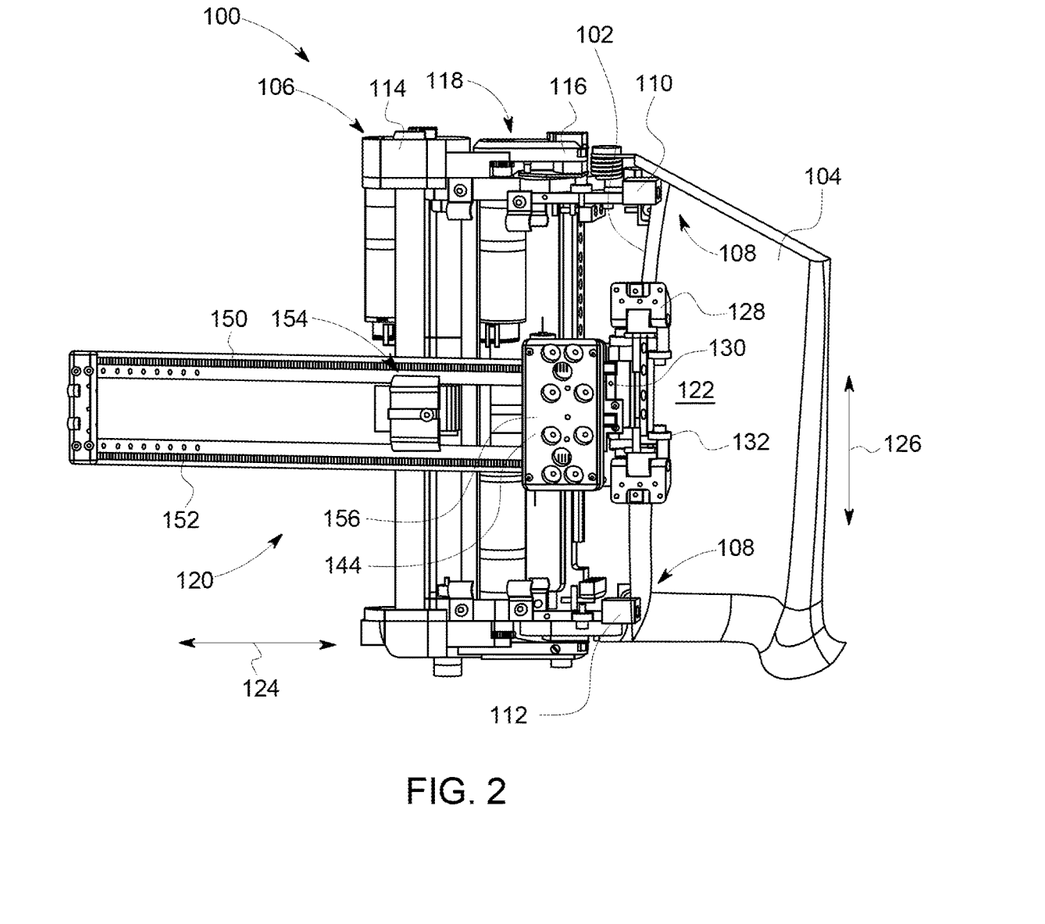
FIG. 2 depicts a scanner attached to a blade according to an embodiment.

FIGS. 2-8 depict systems and methods for inspecting a blade or vane in a turbomachine, such as a compressor or turbine in a gas turbine engine. Any industrial or aviation turbomachine may be inspected. As depicted in FIG. 2, a scanner 100 may be attachable to a trailing edge 102 of a blade 104. In certain embodiments, the scanner 100 may include a main body 106 having a clamp 108 attachable to the trailing edge 102 of the blade 104. In some instances, the clamp 108 may include two clamps attachable to opposite ends of the trailing edge 102 of the blade 104. For example, a first clamp 110 may be attached to a radially outer portion of the trailing edge 102 of the blade 104, and a second clamp 112 may be attached to a radially inner portion of the trailing edge 102 of the blade 104. The first clamp 110 and the second clamp 112 may open and close on the trailing edge 102 of the blade 104 in order to secure the scanner 100 thereto.

Figure 5:
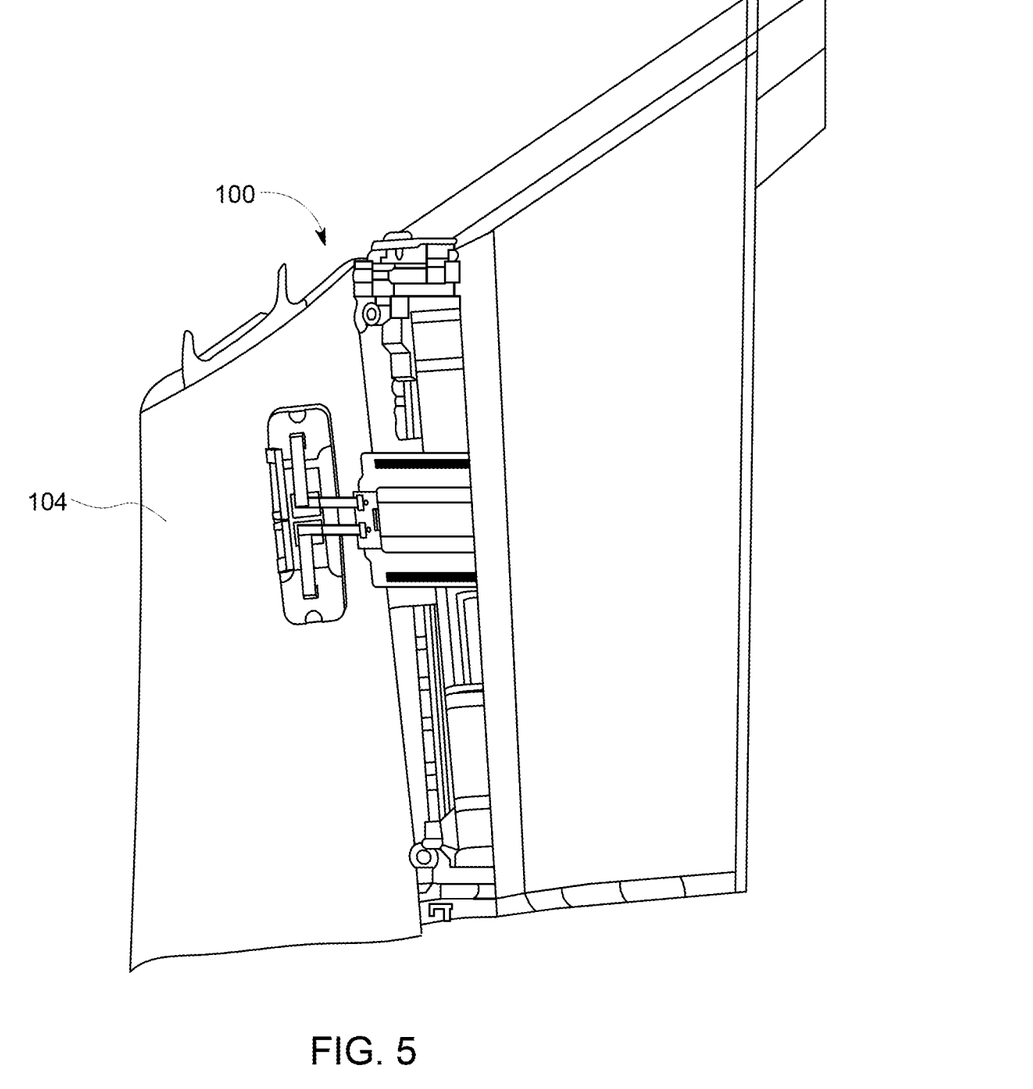
FIG. 5 depicts a scanner attached to a blade according to an embodiment.

In some instances, the main body 106 may be a segmented structure. That is, the main body 106 may include a number of segments pivotally attached together. For example, a first segment 114 may be attached to a second segment 116 via a pivot 118 such that the first segment 114 pivots relative to the second segment 116. The main body 106 many include any number of segments. The segments may be any suitable size, shape, or configuration. As a result, the segmented structure of the main body 106 may enable the scanner to be maneuvered and operated between the various stages of the turbomachine to a desired location, as depicted in FIG. 5.

The scanner 100 may include a first arm 120 moveably attached to the main body 106. In some instances, the first arm 120 may be flexible. In one example, the first arm 120 may be made of spring steel so as to flex about a profile of the blade 104. For example, the first arm 120 may bend about the contour of a first side 122 of the blade 104. The first arm 120 may be any suitable size, shape, or configuration. As noted above, the first arm 120 may move relative to the main body 106. For example, the first arm 120 may move in the axial direction, as indicated by the arrow 124. In addition, the first arm 120 may move in the radial direction, as indicated by the arrow 126.

The first arm 120 may include a first probe 128 attached to an end thereof. Any number of probes may be used. For example, the first arm 120 may include an upper probe disposed radially outward of a lower probe. In this manner, the scanner 100 may include four total probes, such as an upper and a lower eddy current probe for each side of the blade or vane. The wall thickness of the component may vary radially, and thus may require a different probe to inspect the lower part of a blade/vane than for the upper part. Also surface coverage and radial reach may be affected by the specific probe configuration. The probes may be attached to the probe holder using a set of passive joints to provide a gimbal (e.g., allow the probes to adapt to the blade/vane surface geometry). A probe holder may hold a number of probes.

In some instances, the first probe 128 may be pivotally attached to the first arm 120 via a pivot 130. The first probe 128 may be moved about the first side 122 (e.g., the pressure side) of the blade 104 to inspect the blade 104. For example, the first probe 128 may slide about the first side 122 of the blade 104 about one or more rollers 132 as the first arm 120 moves the first probe 128 in the radial 126 and/or axial 124 directions. In this manner, the first probe 128 may be moved about any location on the surface of the first side 122 of the blade 104. In certain embodiments, the rollers 132 may be omitted. In some instances, the first probe 128 may use eddy current or ultrasonic sensors to inspect the blade. The first probe 128 may be any suitable size, shape, or configuration. The first probe 128 may include any type of sensor, camera, or the like.

Figure 4:
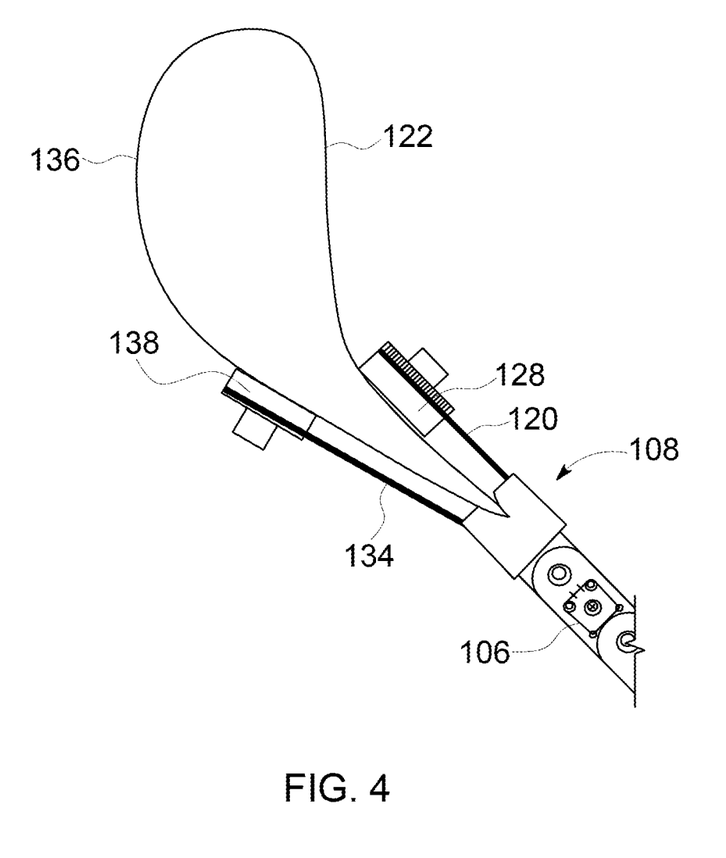
FIG. 4 depicts a scanner attached to a blade according to an embodiment.
Figure 7:
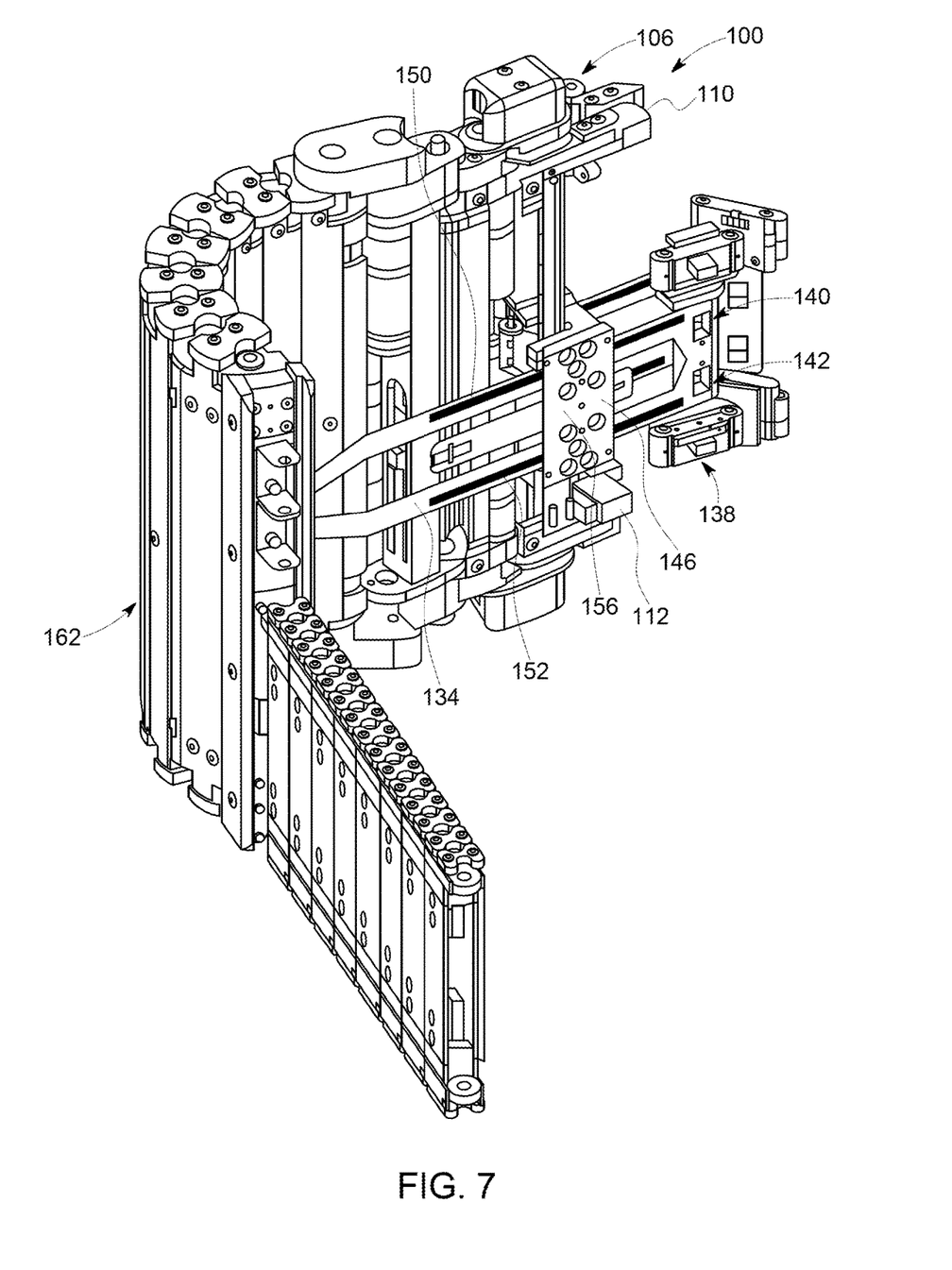
FIG. 7 depicts a scanner attachable to a robotic vehicle according to an embodiment.

As depicted in FIGS. 4 and 7, the scanner 100 may include a second arm 134 moveably attached to the main body 106. In some instances, the second arm 134 may be flexible. In one example, the second arm 134 may be made of spring steel so as to flex about a profile of the blade 104. For example, the second arm 134 may bend about the contour of a second side 136 of the blade 104. The second arm 134 may be any suitable size, shape, or configuration. As noted above, the second arm 134 may move relative to the main body 106. For example, the second arm 134 may move in the axial direction 124. In addition, the second arm 134 may move in the radial direction 126.

The second arm 134 may include a second probe 138 attached to an end thereof. Any number of probes may be used. For example, the second arm 134 may include an upper probe disposed radially outward of a lower probe. In this manner, the scanner 100 may include four total probes, such as an upper and a lower eddy current probe for each side of the blade or vane. The wall thickness of the component may vary radially, and thus may require a different probe to inspect the lower part of a blade/vane than for the upper part. Also surface coverage and radial reach may be affected by the specific probe configuration. The probes may be attached to the probe holder using a set of passive joints to provide a gimbal (e.g., allow the probes to adapt to the blade/vane surface geometry). A probe holder may hold a number of probes. In some instances, the second probe 138 may be pivotally attached to the second arm 138 via a pivot 140. The second probe 138 may be moved about the second side 136 (e.g., the suction side) of the blade 104 to inspect the blade 104. For example, the second probe 138 may slide about the second side 136 of the blade 104 about one or more rollers 142 as the second arm 134 moves the second probe 138 in the radial 126 and/or axial 124 directions. In this manner, the second probe 138 may be moved about any location on the surface of the second side 136 of the blade 104. In certain embodiments, the rollers 142 may be omitted. In some instances, the second probe 138 may use eddy current or ultrasonic sensors to inspect the blade 104. The second probe 138 may be any suitable size, shape, or configuration. The second probe 138 may include any type of sensor, camera, or the like.

As depicted in FIGS. 2 and 7, the scanner 100 may include a first axial actuator 144 in mechanical communication with the first arm 120, a second axial actuator 146 in mechanical communication with the second arm 134, and a radial actuator 148 in mechanical communication with the first arm 120 and the second arm 134. In this manner, the first arm 120 and the second arm 134 may move in unison in the radial direction 126. That is, a single actuator (i.e., the radial actuator 148) may move the first arm 120 and the second arm 134 at the same time. The first arm 120 and the second arm 134, however, may be capable of moving in the axial direction 124 independently of each other. That is, the first axial actuator 144 may move the first arm 120 in the axial direction 124, and the second axial actuator 146 may move the second arm 134 in the axial direction 124. In this manner, the first probe 128 and the second probe 138 may move separately or in parallel in the axial direction 126. In other instances, the first arm 120 and the second arm 134 may include respective radial actuators for independent and separate movement thereof in the radial direction 126. The scanner 100 configuration enables the pressure side and the suction side of the blade 104 to be inspected at the same time. That is, the first probe 128 and the second probe 138 may move along the respective surface of the blade at the same time.

The various actuators discussed herein, including the first axial actuator 144, the second axial actuator 146, and the radial actuator 148, may be in electrical communication with one or more controllers. In addition, one or more sensors and/or probes may be in electrical communication with the controllers. The controllers may be located onboard of the scanner 100 or remotely located. For example, the scanner 100 may be hardwired or wirelessly connected over a network to one or more computing devices and/or controllers for controlling the actuation of the various components of the scanner 100. The one or more computing devices and/or controllers may be located on the scanner 100 or remote thereof. The locations of the first probe 128 and the second probe 138 may be verified by one or more sensors (e.g., proximity sensors) located on the scanner 100. For example, the scanner may include integrated sensors (e.g. proximity sensors, encoders, cameras etc.) used to reconstruct the position of the probes on the blade and/or vanes. In addition, as discussed below, one or more calibration methods may be performed periodically to ensure the scanner 100 operates as intended and that the location of the first probe 128 and the second probe 138 is correct.

In certain embodiments, the first axial actuator 144 and the second axial actuator 146 may be linear track actuators. For example, the first axial actuator 144 may include a first track 150, and the second axial actuator 146 may include a second track 152. The first track 150 and the second track 152 may be disposed in a respective groove 154 in the first segment 114 of the main body 106. The first track 150 and the second track 152 may move in the axial direction 124 via a respective motor 156 disposed on the second segment 116 of the main body 106. Any suitable type and number of actuators may be used herein.

Figure 3:
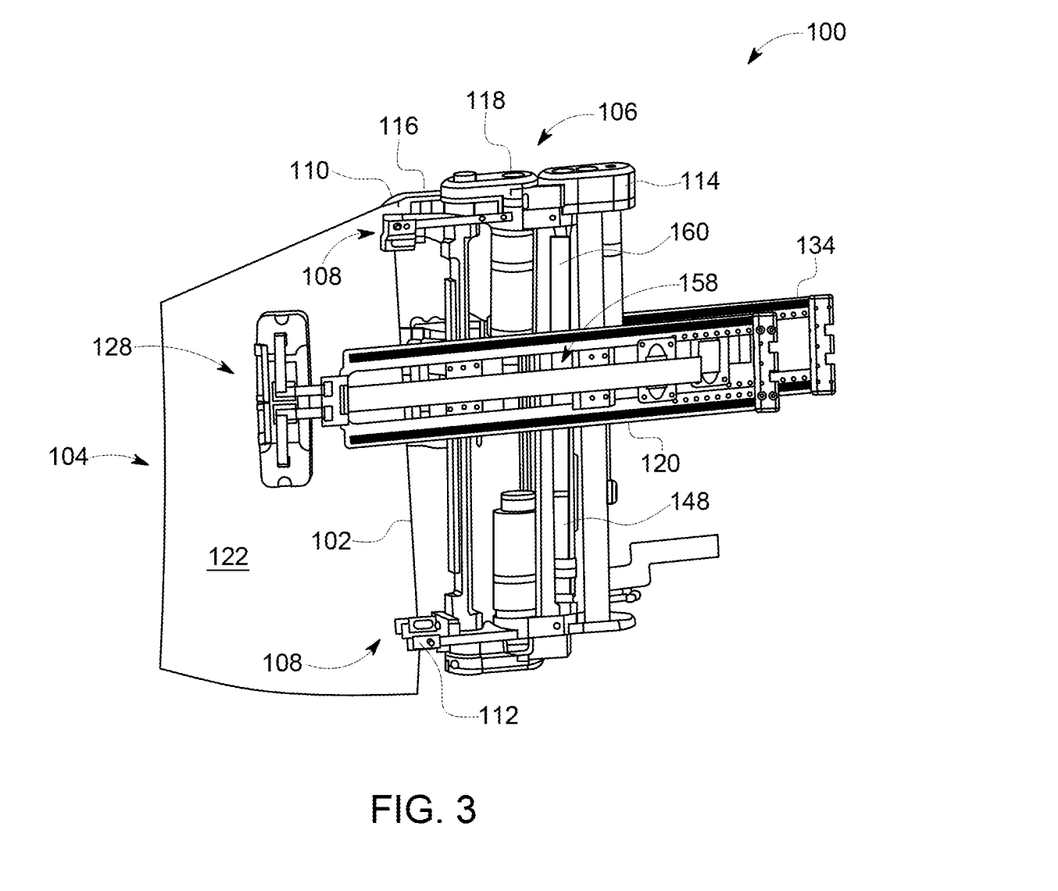
FIG. 3 depicts a scanner attached to a blade according to an embodiment.
Figure 6:
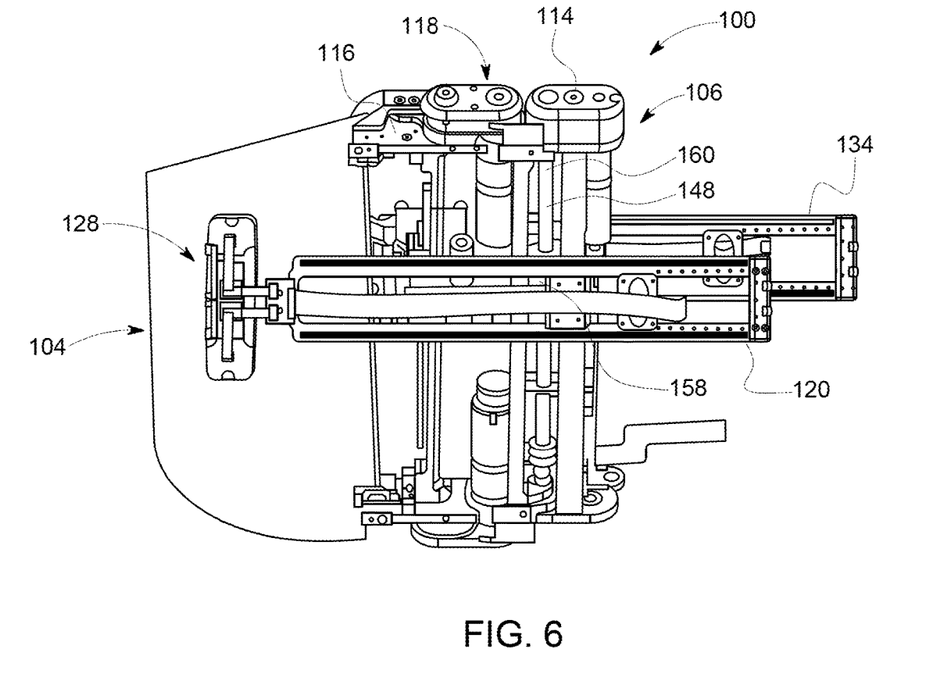
FIG. 6 depicts a scanner attached to a blade according to an embodiment.

In certain embodiments, the radial actuator 148 may be a linear screw actuator. For example, the first arm 120 and the second arm 134 may include a nut 158 attached to a rotatable screw shaft 160, as depicted in FIGS. 3 and 6. In this manner, as the rotatable screw shaft 160 rotates, the first arm 120 and the second arm 134 may move up and down along the rotatable screw shaft 160 in the radial direction 126. Any suitable type and number of actuators may be used herein.

Figure 8:
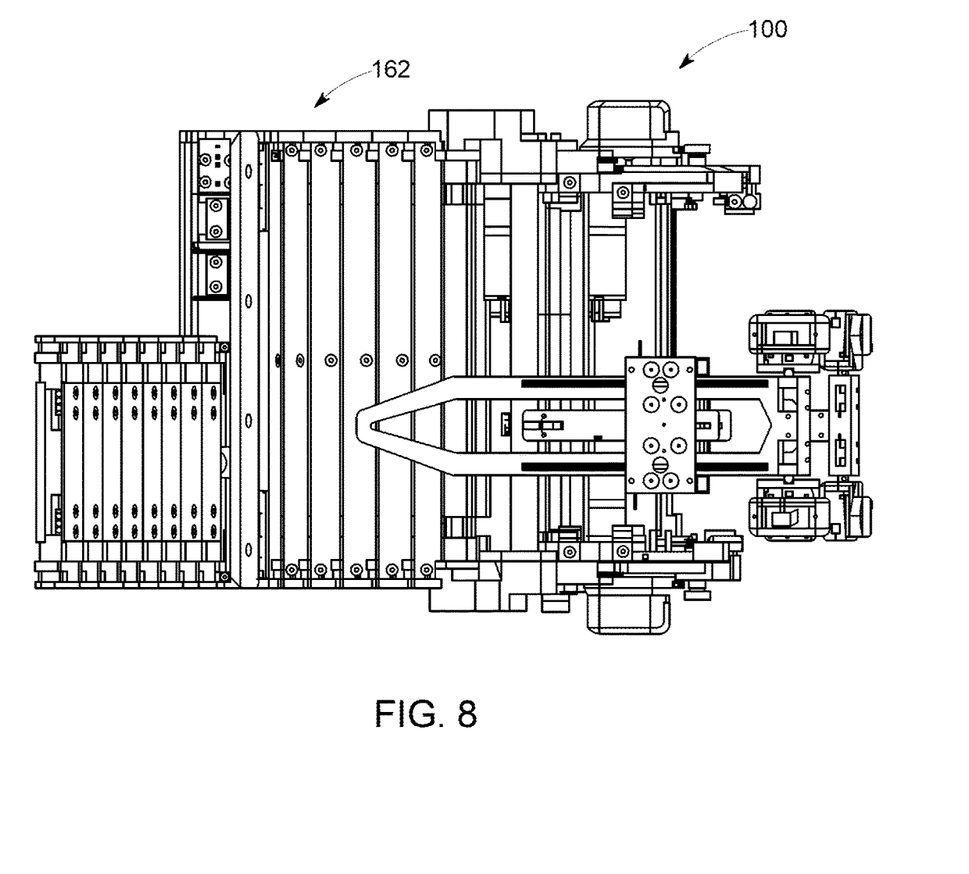
FIG. 8 depicts a scanner attachable to a robotic vehicle according to an embodiment.
Figure 9:
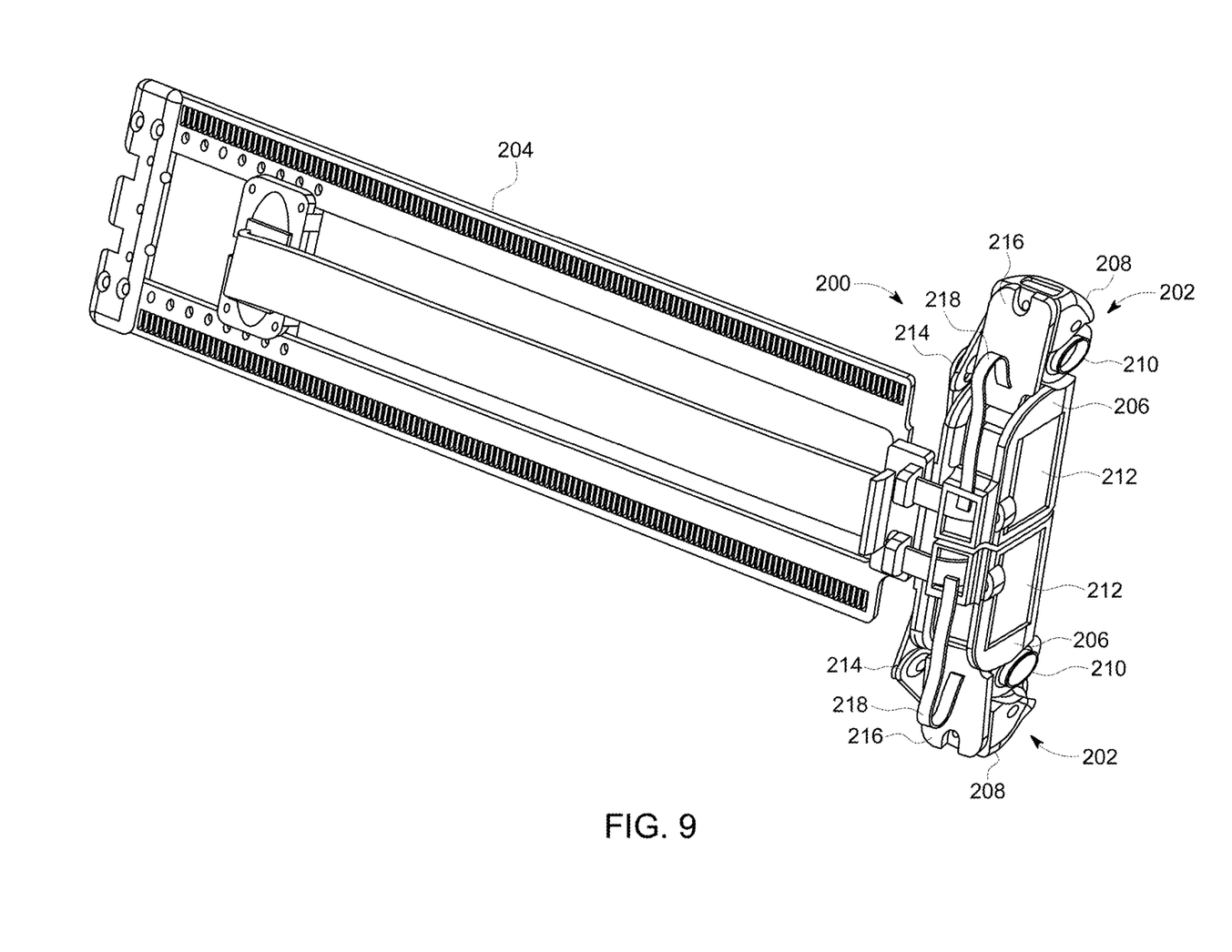
FIG. 9 depicts a liftoff mechanism according to an embodiment.
Figure 10:
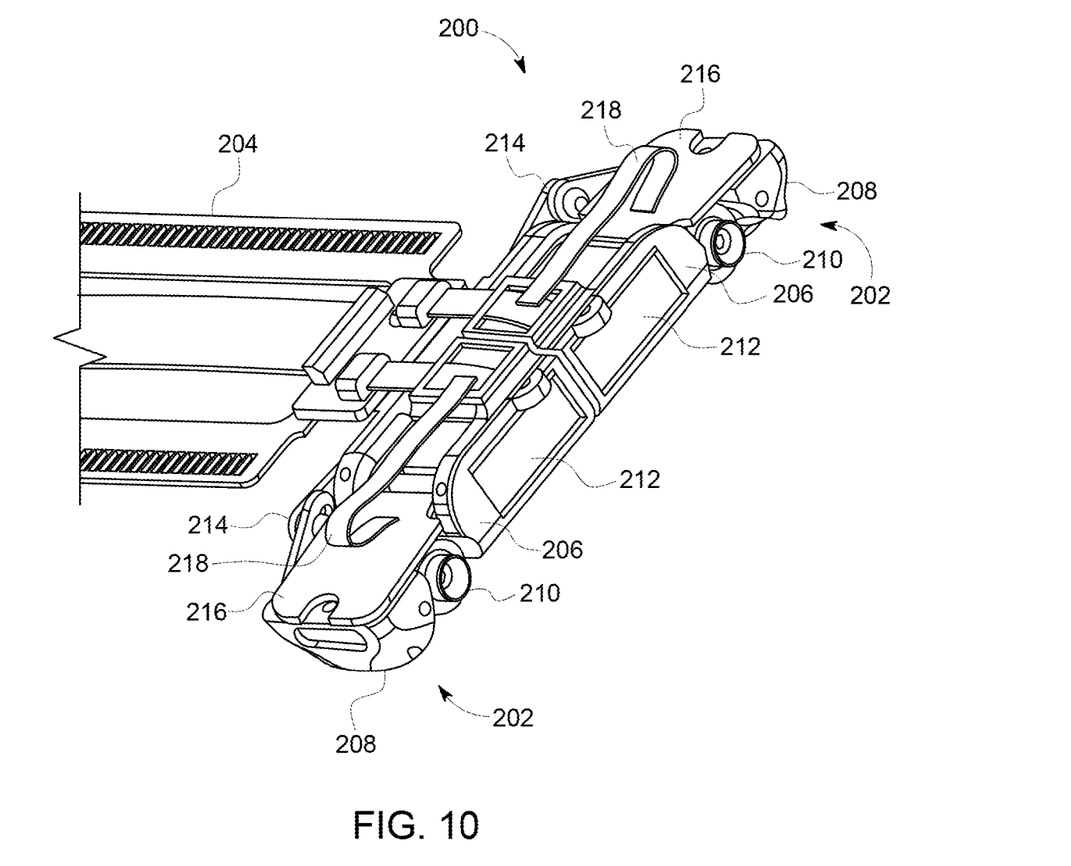
FIG. 10 depicts a liftoff mechanism according to an embodiment.
Figure 11:
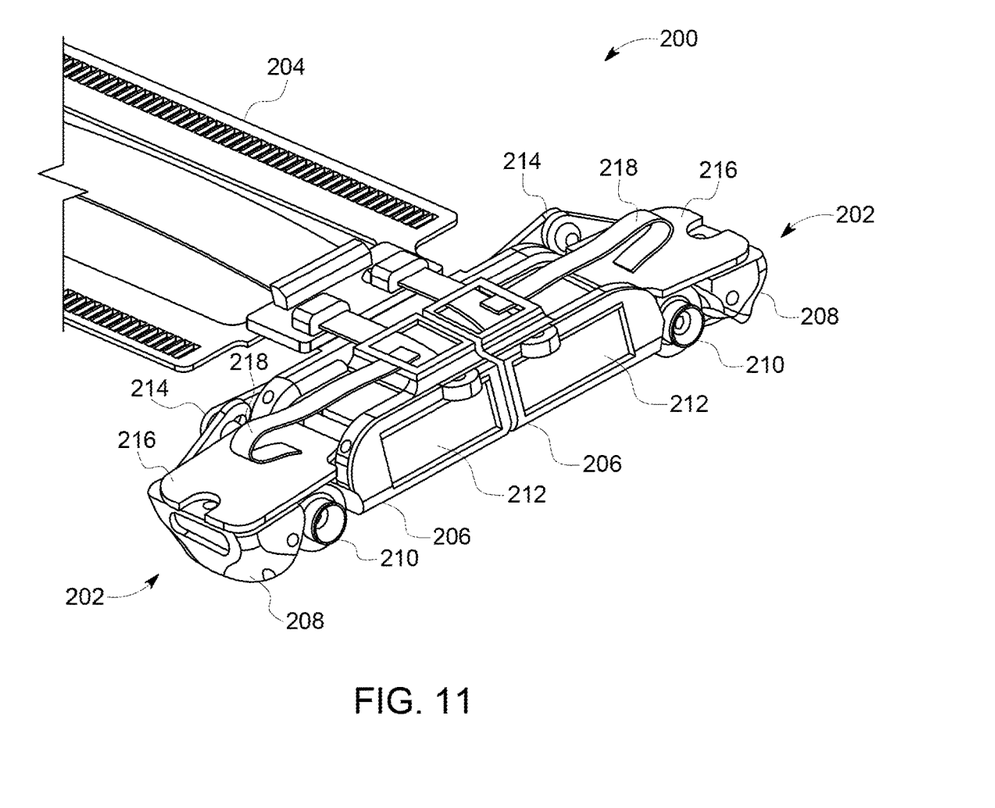
FIG. 11 depicts a liftoff mechanism according to an embodiment.

FIGS. 7 and 8 depict the scanner 100 attached to a robotic device 162, e.g., a robotic vehicle (also known as a scanner deployment device) configured to maneuver the scanner 100 between the various stages of the turbomachine to a desired location. In this manner, the scanner 100 may be maneuvered through the various stages of the compressor or turbine to a desired location adjacent to a blade or vane to be inspected. Once there, the scanner 100 may be attached to the blade or vane. In some instances, the scanner may be detached from the deployment device once attached to the blade and/or vane. In such instances, the deployment device may retract and deploy other scanners to other blades and/or vanes. In other instances, the scanner may be attached to the deployment device during the entire inspection process. Once attached to the blade and/or vane, the arms may move the probes about the pressure and suction side surfaces of the blade or vane. The scanner 100 enables the blades or vanes to be inspected without having to dismantle the turbomachine. Instead, the scanner 100 may, for example, be inserted into and traverse along the hot gas path of a turbine or compressor to the blades or vanes to be inspected.

FIGS. 9-14 depict an example embodiment of a liftoff mechanism 200 for moving (i.e., pivoting) one or more probes 202 attached to an arm 204 between a first configuration and a second configuration in order to calibrate the probes 202. In some instances, the liftoff mechanism 200 may be incorporated into the embodiments disclosed in FIGS. 1-8. That is, the arm 204 and probes 202 may be employed as the first arm 128, the second arm 134, the first probe 128, and/or the second probe 138.

Figure 14:
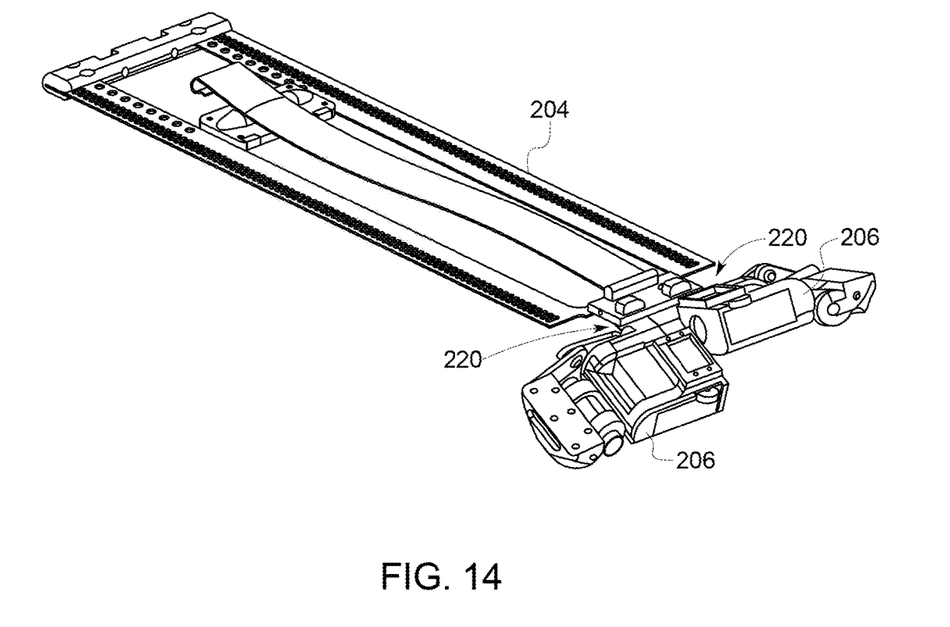
FIG. 14 depicts a liftoff mechanism according to an embodiment.

The probes 202 may include a main body 206 and a probe portion 208. In certain embodiment, the main body 206 may be pivotally attached to the arm 204. For example, as depicted in FIG. 14, the pivot joints 220 may enable each individual main body 206 to pivot relative to the arm 204 independent of the other main body 206. In some instances, the pivot joints 220 may be passive spring loaded joints for maintaining the probe portions in contact with a surface of the blade and/or vane. In some instances, the probe portion 208 may include one or more probes or sensors that may be movably attached to the main body 206 via a pivot 210. That is, the probe portion 208 may pivot relative to the main body 206 about the pivot 210. In order to pivot the probe portion 208, each probe 202 may be in mechanical communication with an actuator, such as a motor 212. In some instances, the motor 212 may comprise a pulse-width modulation (PWM) servo motor. Any suitable actuator may be used herein. In certain embodiment, the motor 212 may be integrated into the main body 206 of the probe 202. That is, the motor 212 may be disposed or housed within the main body 206.

Figure 12:
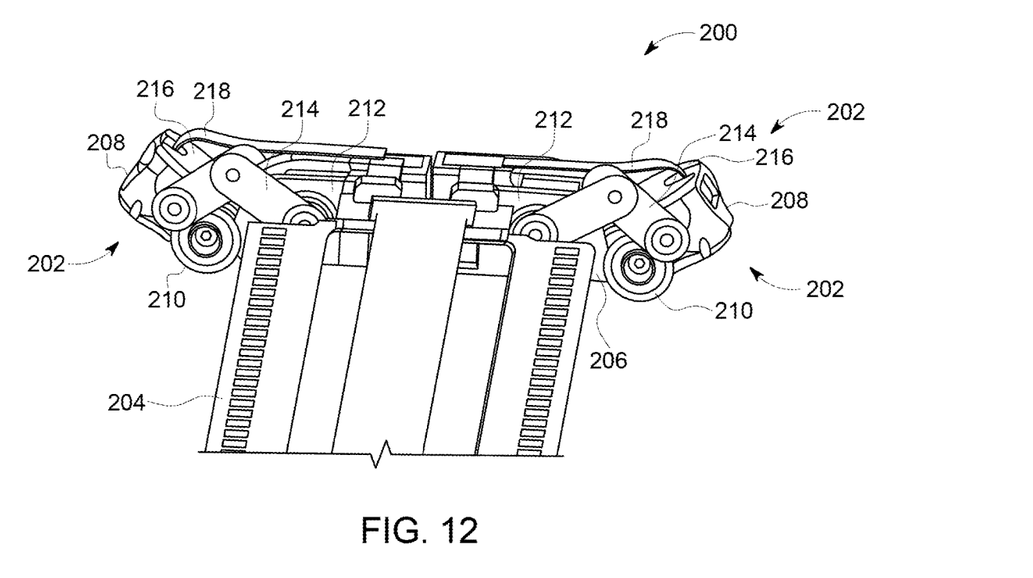
FIG. 12 depicts a liftoff mechanism according to an embodiment.
Figure 13:
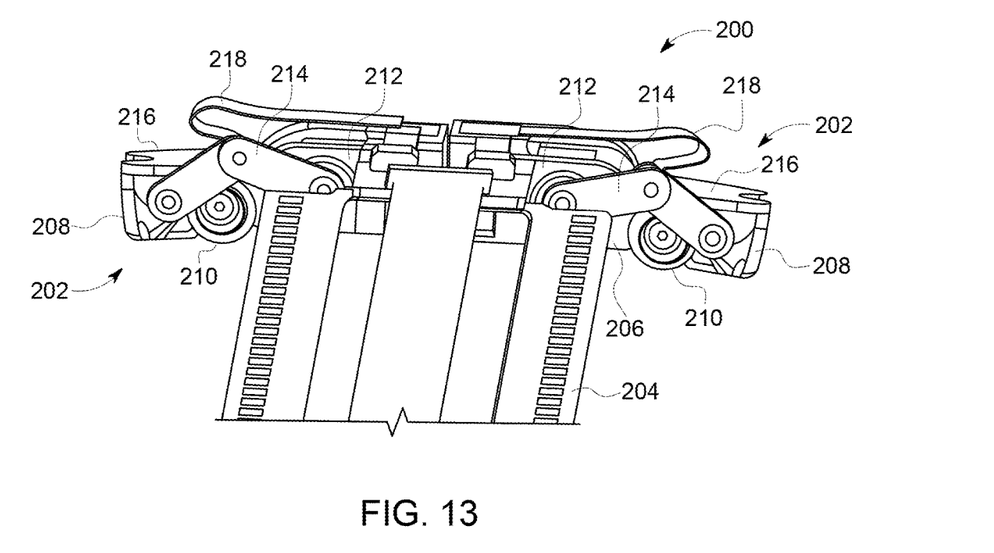
FIG. 13 depicts a liftoff mechanism according to an embodiment.

In certain embodiments, the motor 212 may be attached to the probe portion 208 via a linkage 214. When the motor 212 is activated, it may move the linkage 214, which in turn may pivot the probe portion 208 about the pivot 210 between a first configuration (as depicted in FIG. 13) and a second configuration (as depicted in FIG. 12). In the first configuration, the probe portion 208 may be in contact with (or "on") the surface of the blade or vane. Conversely, in the second configuration, the probe portions 208 may not be in contact with (or "off") the surface of the blade or vane. In this manner, the motor 212 and linkage 214 may pivot the probe portion 208 about the pivot 210 between the on and off positions.

As noted above, the liftoff mechanism 200 may enable the calibration of the probes 202. For example, calibrating the probes 202 may involve collecting a series of electrical signals with the probes 202 in the first configuration (i.e., "on" the surface of the blade or vane) and in the second configuration (i.e., "off" the surface of the blade or vane) both before, during, and after operation of the scanner 100. Following an analysis of the "on" and "off" electrical signals, calibration settings may then be determined. The calibration procedure is designed to set the sensitivity of the probes 202 so that the subsequent readings are more accurate in determining inclusions or damages to the blade or vane surfaces. In some instances, the calibration of the probes 202 may be checked in the "off" configuration after operation of the scanner 100 to enable an operator to determine if the scanner 100 has performed constantly throughout the blade or vane inspection by comparing any difference between the before and after calibration readings.

The probes 202 may include printed circuit boards 216 (PCBs) for providing electrical pathways from the probes 202 to a controller or the like. The PCBs 216 may be in electrical communication with one another and/or a controller via one or more electrical connections 218. Due to the pivoting movement of the probes 202, the electrical connections 218 may comprise flexible wires or the like.

In this manner, as noted above, each probe 202 may be movable independently due to the activation of various actuators and the changing surface of the blade or vane geometry. More so, in order to calibrate the probes 202 when in the "off" position (i.e., away from the surface of the blade or vane), the servo motor 212 may be activated via a controller to rotate the linkage 214, which may pivot and "lift" the probe portion 208 away from the blade or vane surface, as shown in FIG. 12. Once the calibration signal is recorded in the "off" configuration, the servo motor 212 may return to its start position, which may pivot the probe portion 208 to reengage the blade or vane surface, as shown in FIG. 13. The liftoff mechanism 200 enables a user to execute a remote calibration procedure before and after every blade or vane inspection.

It should be apparent that the foregoing relates only to certain embodiments of the present application and the resultant patent. Numerous changes and modifications may be made herein by one of ordinary skill in the art without departing from the general spirit and scope of the invention as defined by the following claims and the equivalents thereof. Although embodiments have been described in language specific to structural features and/or methodological acts, it is to be understood that the disclosure is not necessarily limited to the specific features or acts described. Rather, the specific features and acts are disclosed as illustrative forms of implementing the embodiments.

That which is claimed:

1. A scanner for inspecting a component, the scanner comprising:
    a main body comprising a clamp attachable to the component;
    a first arm moveably attached to the main body, wherein the first arm is flexible;
    a first probe attached to the first arm;
    a first axial actuator in mechanical communication with the first arm; and
    a radial actuator in mechanical communication with the first arm.

2. The scanner of claim 1, the scanner comprising:
    a second arm moveably attached to the main body;
    a second probe attached to the second arm; and
    a second axial actuator in mechanical communication with the second arm,
    wherein the radial actuator is in mechanical communication with the second arm.

3. The scanner of claim 2, wherein the second probe is pivotally attached to the second arm.

4. The scanner of claim 2, wherein the second arm is flexible.

5. The scanner of claim 2, wherein the second axial actuator is a linear track actuator.

6. The scanner of claim 2, further comprising a liftoff mechanism in mechanical communication with the first probe, the second probe, or a combination thereof for calibrating the first probe, the second probe, or a combination thereof.

7. The scanner of claim 1, wherein the main body comprises a segmented structure.

8. The scanner of claim 7, wherein the segmented structure comprises a plurality of segments pivotally attached together.

9. The scanner of claim 1, wherein the clamp comprises two clamps attachable to a trailing edge of the component.

10. The scanner of claim 1, wherein the first probe is pivotally attached to the first arm.

11. The scanner of claim 1, wherein the first axial actuator is a linear track actuator.

12. The scanner of claim 1, wherein the radial actuator is a linear screw actuator.

13. A scanner for inspecting a component, the scanner comprising:
    a main body comprising a clamp attachable to a trailing edge of the component;
    a first flexible arm moveably attached to the main body about a first side of the component;
    a first probe pivotally attached to the first flexible arm, wherein the first probe is configured to slide along the first side of the component;
    a first axial actuator in mechanical communication with the first flexible arm;
    a second flexible arm moveably attached to the main body about a second side of the component;
    a second probe pivotally attached to the second flexible arm, wherein the second probe is configured to slide along the second side of the component;
    a second axial actuator in mechanical communication with the second flexible arm; and
    a radial actuator in mechanical communication with the first flexible arm and the second flexible arm.

14. The scanner of claim 13, wherein the main body comprises a plurality of segments pivotally attached together.

15. The scanner of claim 13, wherein the clamp comprises two clamps attachable to a trailing edge of the component.

16. The scanner of claim 13, wherein the first axial actuator and the second axial actuator are linear track actuators.

17. The scanner of claim 13, wherein the radial actuator is a linear screw actuator.

18. The scanner of claim 13, further comprising a liftoff mechanism in mechanical communication with the first probe, the second probe, or a combination thereof for calibrating the first probe, the second probe, or a combination thereof.

19. A method for inspecting a component, the method comprising:
    positioning a main body adjacent to the component;
    moving a first arm with a first probe and a second arm with a second probe in a radial direction with a radial actuator;
    moving the first arm and the first probe in an axial direction with a first axial actuator;
    moving the second arm and the second probe in the axial direction with a second axial actuator; and
    calibrating the first probe, the second probe, or a combination thereof by pivoting the first probe, the second probe, or a combination thereof with a liftoff mechanism.

20. The method of claim 19, further comprising clamping the main body to the component.

21. The method of claim 19, further comprising:
    pivoting the first probe about the first arm; and
    pivoting the second probe about the second arm.

22. The method of claim 19, further comprising pivoting one or more segments of the main body.

* * * * *